United States Patent [19]

Morse et al.

[11] Patent Number: 5,030,215
[45] Date of Patent: Jul. 9, 1991

[54] PREPARATION OF FIBRINOGEN/FACTOR XIII PRECIPITATE

[75] Inventors: Brenda S. Morse, Chamblee; A. Denise Turner, Dunwoody; John F. Carpenter, Marietta, all of Ga.

[73] Assignee: CryoLife, Inc., Marietta, Ga.

[21] Appl. No.: 460,640

[22] Filed: Jan. 3, 1990

[51] Int. Cl.⁵ ............................................. B65D 35/22
[52] U.S. Cl. ................................. 604/410; 604/416; 604/408
[58] Field of Search .............. 604/403, 408, 409, 410, 604/415, 416, 4, 7

[56] References Cited

U.S. PATENT DOCUMENTS

| | | | |
|---|---|---|---|
| 3,545,671 | 12/1970 | Ross | 422/44 |
| 3,870,042 | 3/1975 | Viguier | 604/406 |
| 3,911,918 | 10/1914 | Turner | 604/410 |
| 3,985,135 | 10/1976 | Carpenter et al. | 604/410 |
| 3,986,506 | 10/1976 | Garber et al. | 604/410 X |
| 4,006,745 | 2/1977 | Sorenson et al. | 604/4 |
| 4,298,598 | 11/1981 | Schwarz | 424/94.64 |
| 4,406,886 | 9/1983 | Bier | 530/383 |
| 4,453,939 | 6/1984 | Zimmerman | 604/368 |
| 4,608,178 | 8/1986 | Johansson | 210/744 |
| 4,627,879 | 12/1986 | Rose et al. | 424/448 X |
| 4,714,457 | 12/1987 | Alterbaum | 494/37 |
| 4,857,190 | 8/1989 | Wada et al. | 210/232 |

OTHER PUBLICATIONS

Schlag and Redhl (eds) Fibrin Sealant in Operative Medicine, vol. 1-7 Springer-Verlag, Heidelberg (Table of Cont.) Dresdale et al, Ann. Thorac. Surg. 40:385 (1985).
Lupinetti et al, J. Thorac. Cardiovasc. Surg., 90:502 (1985).
Marx, G., Arch. Brochem. Biophys. 266:285 (1988).
Dresdale et al, Surgery 97:750 (1985).
Siedentop et al, Laryngoscope 96:1062 (1986).
Weisman et al, Larynoscope 97:1186 (1987).
Vila et al, Thrombosis Research 59:651 (1985).
Blomback et al, Arkiv for Kemi, band 10 nr 29 pp. 415-443 (1956).
Wallenbeck et al, Thrombosis Research 6:75 (1975).
Straughn et al, Throm. Diath. Haemorrh. 16:198 (1966).
Mosesson et al, Biochemistry 5:2829-2835 (1966).
Spotnitz et al, The American Surgeon 53:460 (1987).
Marx et al, Am. J. Hematology 19:151 (1985).
Marx, Am. J. Hematology 27:104-109 (1988).
Maeda et al., Int. J. Biol. Mioromol. 5:159 (1983).
Dresdale et al, Ann. Thorac. Surg. 40:385 (1985).

Primary Examiner—Robert A. Hafer
Assistant Examiner—Kevin G. Rooney
Attorney, Agent, or Firm—Cushman, Darby & Cushman

[57] ABSTRACT

The present invention relates to a system for use in the preparation of autologous or single-donor fibrin sealant. The invention further relates to a method of preparing fibrin sealant.

37 Claims, 3 Drawing Sheets

PREPARATION OF FIBRINOGEN/FACTOR XIII PRECIPITATE

BACKGROUND OF THE INVENTION

1. Field of the Invention

The present invention relates to a system for use in the preparation of autologous or single-donor fibrin sealant. The invention further relates to a method of preparing fibrin sealant.

2. Background Information

The blood coagulation system is a complex series of proteins and factors which are activated sequentially to produce an insoluble fibrin mass or clot. In the final stages of the process, fibrinogen is cleaved by thrombin to generate fibrin monomer, which rapidly polymerizes and is crosslinked by activated Factor XIII to form an insoluble matrix.

Preparations of human coagulation factors including fibrinogen and thrombin, have been used extensively in surgery over the last ten years [Schlag G. and Redl (eds) Fibrin Sealant in Operative Medicine - Thoracic-Cardiovascular Surgery, vol. 1-7 Springer-Verlag, Heidelberg]. These biological fibrin sealants promote hemostasis and wound healing by sealing leakage from tissues, sutures, staples, and prostheses and are particularly useful during open heart surgery in heparinized patients. The sealants also have limited use as an adhesive for the bonding of tissues and they reduce the amount of blood required for transfusions by controlling intraoperative bleeding. Their effectiveness is reflected in the extensive range of surgical applications for which they have been used, including cardiovascular surgery, plastic surgery, orthopedics, urology, obstetrics and gynecology, dentistry, maxillofacial and opthalmic surgery.

Fibrin sealant products prepared from pooled human plasma are available commercially in Europe (Tissucol/Tisseel, Immuno AG, Vienna, Austria and Beriplast P, Hoechst, West Germany) but have not received U.S. Food and Drug Administration approval, probably due to possible risk of transmission of HIV-1, hepatitis B and other serologically transmitted illnesses.

As an alternative, some hospit.las are preparing fibrin sealant in-house using the patient's own blood (autologous) or single-donor (homologous) plasma as a source of fibrinogen and Factor XIII. The components are typically prepared by freezing plasma at temperatures below −20° C. overnight, slowly thawing the material at 0-4° C., centrifuging, and transferring the cryoprecipitate to a syringe or spray container [Dresdale et al Ann. Thorac. Surg. 40:385(1985); U.S.Pat. No. 4,627,879]. The procedure usually requires several hours, making the product unavailable for emergency cases. The lengthy manipulations currently required to generate fibrin sealant also introduce the risk of contaminating the product and transmitting viral infections to the technician(s) involved.

The thrombin, usually purified from bovine plasma, can be obtained commercially and is typically prepared in a separate syringe or spray container. The two solutions are delivered simultaneously or alternately to generate fibrin sealant at the site of the wound or, alternatively, the sealant is applied to a collagen matrix (e.g. Gelfoam or Avitene) and then pressed against the site [Lupinetti et al. J. Thorac. Cardovasc. Surg. 90:502 (1985); and U.S. Pat. 4,453,939].

SUMMARY OF THE INVENTION

It is a general object of the present invention to provide a system and method for the rapid preparation of autologous fibrin sealant which removes the risk of transmitting infection (especially HIV-1 and hepatitis infections) since the fibrin sealant is made from the patient's own blood components. The system can also be used to prepare fibrin sealant from designated single donors. In addition, the system and method can be used to prepare fibrin sealant from single-donor animals or pooled animal plasma for use in veterinary applications.

It is another object of the present invention to provide a system and a method for the preparation of fibrin sealant in high yield with minimal risk of exposure to the technician and minimal risk of contaminating the blood products.

These and other objects are realized in accordance with the present invention by obtaining blood coagulation or clotting factors from a patient's own blood or from an appropriate donor by use of a system that includes two or more sterile containers connected by sterilized tubing or a single container having two or more compartments defined therewithin. The patient or donor's blood is drawn into one container or compartment of the system. One or more anti-coagulants are present within the first container or compartment and the blood is mixed therewith. The container is then subjected to, for example, centrifugation so as to separate the plasma from red blood cells. The plasma is transferred from the first container or compartment into a second container or compartment of the system. An agent that effects precipitation of the blood coagulation factor(s) is contained within the second container and is mixed with the plasma. The mixture is then subjected to, for example, centrifugation to obtain a coagulation factor-enriched precipitate. The precipitate is retrieved from the second container or compartment and is mixed with a solution of thrombin and calcium to prepare the fibrin sealant. In the alternative, the factor-poor plasma is decanted from the second container or compartment. The precipitate can then be dissolved in a buffer and transferred to a delivery device. Thrombin and, if necessary calcium, are mixed with the fibrinogen/Factor XIII solution to form the fibrin sealant.

Other objects, features and characteristics of the present invention, as well as the methods of operation and functions of the related elements of the structure, and the combination of parts and economies of manufacture, will become more apparent upon consideration of the following detailed description and the appended claims, with reference to the accompanying drawings, all of which form a part of this specification, wherein like reference numerals designate corresponding parts in the various figures.

DETAILED DESCRIPTION OF THE PRESENTLY PREFERRED EXEMPLARY EMBODIMENT

The present invention relates to a method of collecting blood coagulation factors and to a system suitable for use in same.

In one embodiment, the method of the present invention comprises, as a first step, contacting plasma with an amount of zinc ion sufficient to cause precipitation, from the plasma, of fibrinogen and Factor XIII (e.g. 10-100 mM zinc acetate, preferably about 20-40 mM) (Marx Arch. Biochem. Biophys. 266:285 (1988); U.S. Pat. 4,406,886). The zinc ions can be provided as a pharmaceutically acceptable zinc (II) salt (e.g. zinc sulfate or zinc acetate). The precipitated clotting factors are then separated from the factor-poor plasma, for example, by centrifugation (e.g. at 1000-6000xg for 3 to 15 minutes). The precipitate is then immediately dissolved in a pharmaceutically acceptable buffer (e.g. 50 mM Tris-HCl, pH 7.4; 150 mM sodium chloride; 250 mM sodium citrate; 20 mM epsilon-aminocaproic acid and 50 mM arginine; for example about 300 µl of buffer per ml of precipitate), or, alternatively, the precipitate is stored at 0-4° C. for several days or -20° C. or lower for several months prior to dissolution. (Alternatively, a pharmaceutically acceptable copper salt can be used.)

Once dissolved, the fibrinogen and Factor XIII thus prepared can be contacted with thrombin and, where necessary, calcium, under conditions such that a fibrin sealant is formed at a body site (Dresdale et al, Surgery 97:750 (1985). (The term "body site" as used herein includes the tissues in the area of a wound or incision as well as implantable tissues or components to be inserted into the area, e.g., vascular prostheses, bone or collagen pads.)

In a further embodiment, the method of the present invention comprises, as a first step, drawing a blood sample from a patient into a first sterile container having disposed therewithin an effective amount of an anticoagulant. Suitable anticoagulants include citrate-dextrose, heparin, and citrate solutions. In a next step, the plasma of the blood sample is separated, for example, by centrifugation (e.g. at 1000 to 6000 x g for 3 to 15 min.) from red blood cells (RBCs) and other large debris present in the sample. The thus obtained plasma is then transferred to a second sterile container via a conduit attached to an outlet port of the first container and an inlet port of the second container. The plasma is mixed with an amount of a fibrinogen/Factor XIII precipitating agent (present in the second container and/or the conduit) sufficient to effect precipitation of the clotting factors. Suitable precipitating agents include pharmaceutically acceptable zinc (II), copper (II) and ammonium salts, pharmceutically acceptable alcohols (e.g. ethanol), amino acids (e.g. glycine) and polymers (e.g. polyethylene glycol, dextran, or hydroxyethyl starch). (Siedentop et al, Laryngoscope 96:1062 (1986); Weisman et al, Laryngoscope 97:1186 (1987); Mosesson et al, Biochemistry 5:2829 (1966); Villa et al, Thrombosis Research 59:651 (1985); Blomback et al Arkiv for Kemi, band 10 nr 29, pp 415-443 (1956); Wallenbeck et al, Thrombosis Research 6:75 (1975); Straughn et al Throm. Diath. Haemorrh. 16:198 (1966)).

The fibrinogen/Factor XIII-containing precipitate and factor-poor plasma are then separated, for example, by centrifugation (e.g. at 1000 to 6000 ×g for 3-5 min.), the supernatant discarded, and the pellet resuspended in buffer. The coagulation factor-enriched solution can be transferred into a delivery device (e.g. syringe), mixed with thrombin, and the fibrin glue applied to the site of use.

Figure 1:
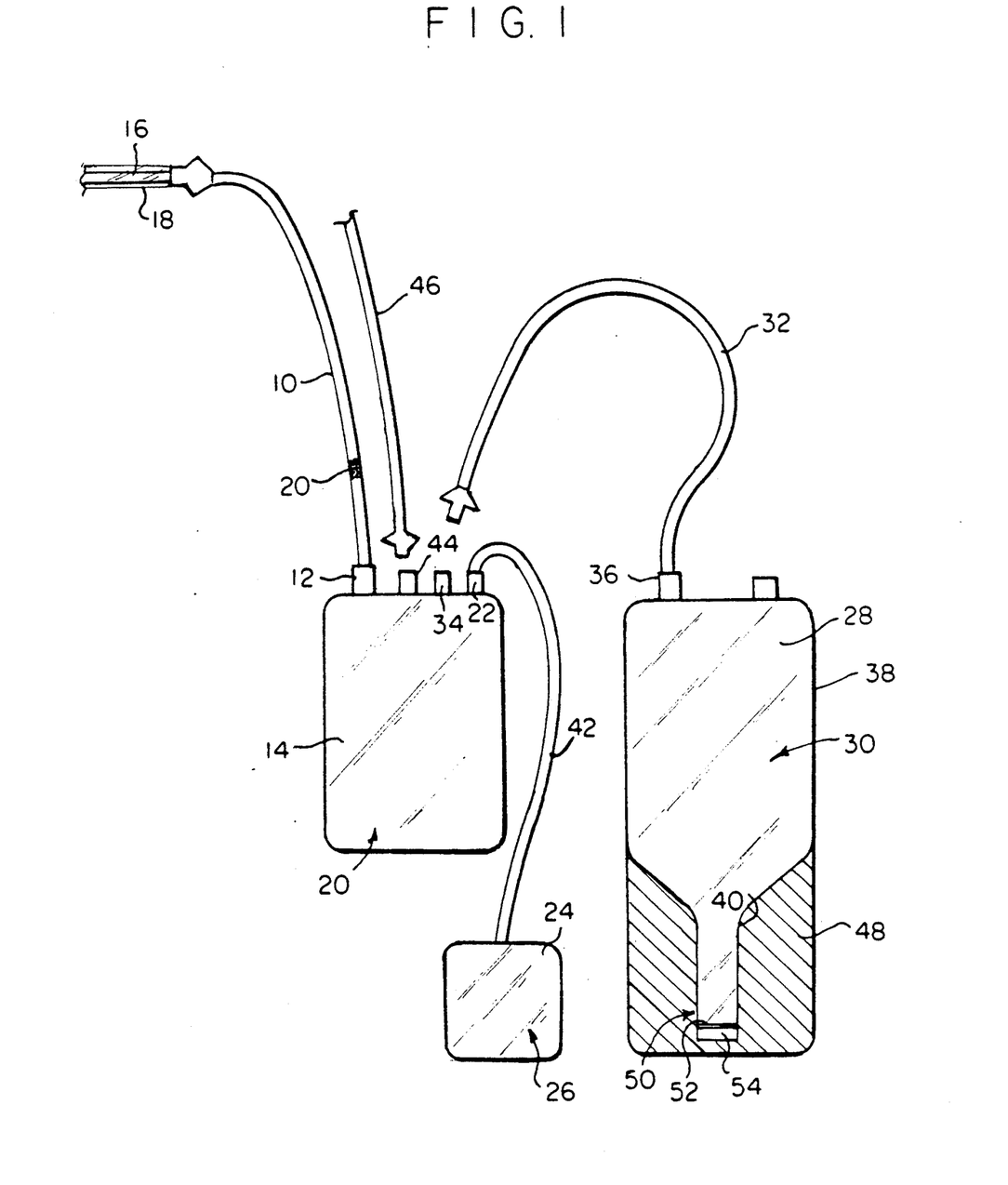
FIG. 1 is a schematic elevational view of a multi-container system provided in accordance with the present invention.
Figure 2:
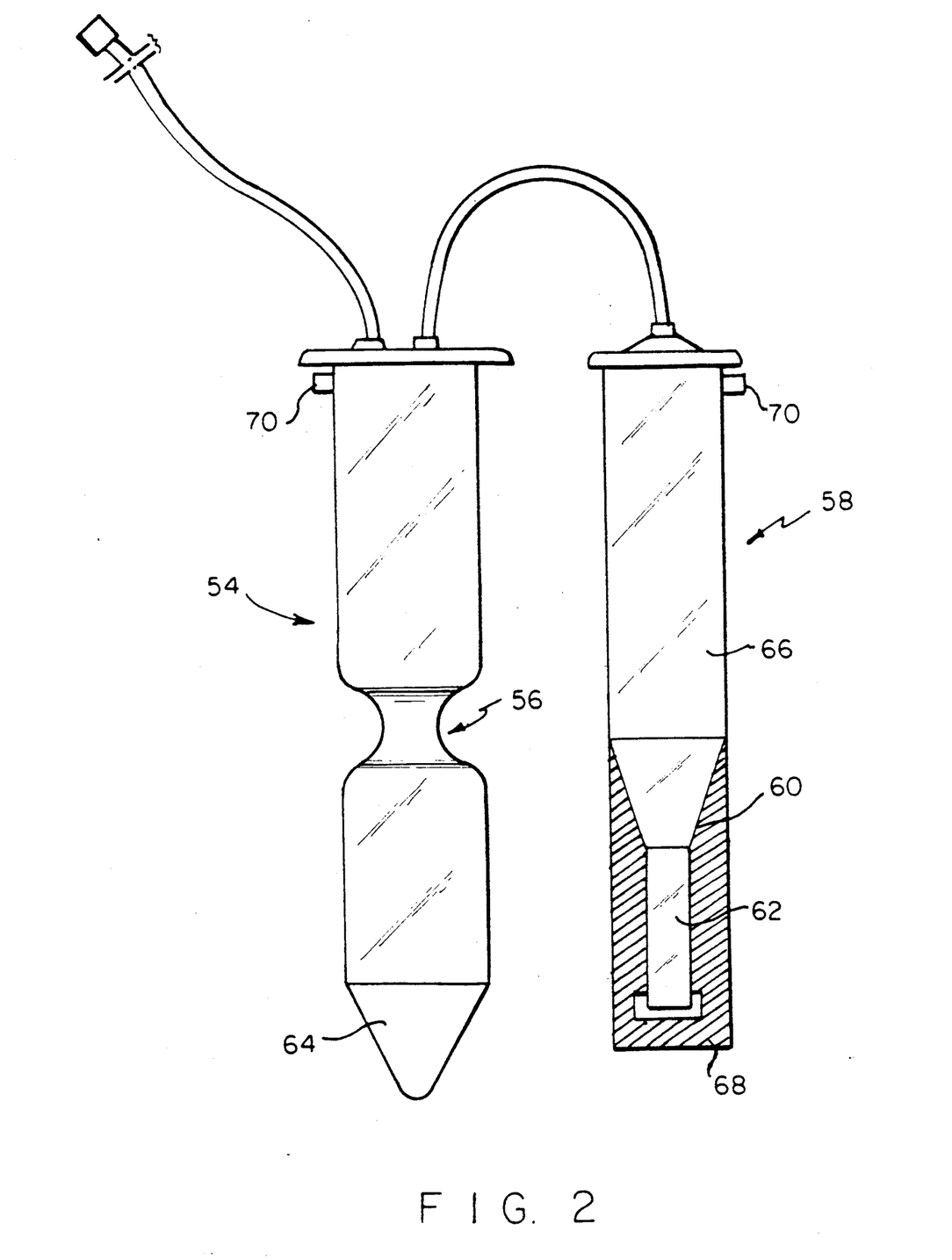
FIG. 2 is a schematic elevational view of an alternate multi-container system provided in accordance with the present invention.

As shown in particular in FIGS. 1 and 2, the system of the present invention can be comprised of two or more sterile closed containers such as, for example, plastic bags, plastic tubes or bottles, glass tubes or bottles, or combinations thereof. As such, the system can be employed for producing autologous or single-donor fibrin sealant which can be used approximately 30 minutes after the blood is first drawn from the patient.

Referring to FIG. I, in accordance with a first embodiment of the present invention, the containers of the system are formed from flexible polyvinyl chloride (PVC) bags (e.g., polyvinyl chloride (PVC)), as shown. Thus, the bags can be similar in form to conventional blood bags.

As shown in FIG. 1, the multi-flexible bag system provided in accordance with the present invention is provided so that, prior to use, a conduit 10 extends between an inlet 12 of a first container 14 and the patient or donor (not shown). A needle 16 for accessing the patient or donor's venous system is defined at a first end of the conduit 10. A cover 18 detachably covers the sterile needle 16. An anticoagulant 20 is disposed within the conduit itself as well as within the bag. The flexible bag 14 is preferably compressed prior to use such that minimal air is present. The bag may be compressed by, for example, withdrawing air from within the container with a suitable syringe or the like coupled to an outlet port of the bag. In the alternative, although not shown in particular, an air or vacuum port can be defined in the bag.

Coupled to a second inlet port 22 of the first container 14 is an auxiliary, preferably flexible, container 24 having a red blood cell stabilizing agent 26 therein, as described more fully below. Typical stabilizing agents include mannitol and adenine.

In the illustrated embodiment, the second container 28 is also formed from a flexible bag. A precipitating agent 30 is provided within the interior of the second container and, prior to use, minimal air is present within that container, the air having been expressed from the container through, for example, an air or suction port (not shown). Precipitating agent 30 is an agent that precipitates blood clotting factors including fibrinogen and Factor XIII. The precipitating agent can be a single compound or combination of components including, as indicated above, amino acids such as glycine or beta-alanine, salts such as zinc salts, copper salts or ammonium sulfate, alcohols such as ethanol. or polymers such as dextran, polyethylene glycol and hydroxyethyl starch. In addition to precipitating agent 30, second container 28 can also contain a protein stabilizing agent such as a sugar (e.g. glucose, fructose or sucrose) or buffer, protease inhibitor such as aprotinin or epsilon-aminocaproic acid, antibiotic and/or additives such as bone chips or factors which promote healing such as hormones, and growth factors (e.g. insulin, platelet-derived growth factor, epithelial factor.). A transfer line 32 is coupled to an outlet port 34 of the first container 14 and an inlet port 36 of the second container for transferring plasma from the first container 14 to the second container 28, as discussed more fully below. One or more internal breakable seals, not shown in particular, is provided in the transfer line 32 to prevent the anti-coagulant solution 20, blood, or plasma from prematurely being transferred to the second container and to prevent the precipitating agent 30 from flowing from the second container 28 to the first container 14. In the alternative, a clamp can prevent undesired flow between the first and second containers.

As can be seen, in the embodiment of FIG. 1, the second container 28 is shaped so as to include a first relatively wide portion 38 and a second relatively narrow throat portion 40 defining an inlet for a precipitate collecting compartment 50, as described more fully below. In the alternative, the second container 28 can include a first relatively large width, a second relatively narrow width defining a throat and a third relatively large diameter portion for receiving precipitate passed through the throat passage. With such a configuration, the narrow throat passage facilitates separation of the precipitate receiving compartment 50 from the remainder of the second container.

With the foregoing flexible bag system, the first step is to obtain whole blood from the patient or donor. Thus, the cover 18 is detached from the sterile needle 16 defined at the first end of conduit 10. Typically, a breakable seal will be defined within the conduit 10 to prevent premature flow from the patient to the bag and likewise to retain anticoagulant 20 within the tube 10 as well as within the container 14. When it is desired to transfer the donor or patient's whole blood into the first container 14, the seal is broken or conduit clamp removed so that blood can flow through the conduit 10 into the bag 14 and mix with the anticoagulant coagulant 20 therewithin. Preferably, the flexible bag 14 is kneaded and/or gently inverted so as to efficiently disperse anticoagulant 20 within the whole blood. Once a sufficient amount of blood has been collected, the conduit 10 is heat sealed or closed utilizing another sterile procedure such as, staples, clamps, or the like and the needle 16 is removed from the patient. The conduit 10 is then sealed and cut or tied in a conventional manner.

The whole blood so collected is then subjected to centrifugation at 1,000 to 6,000 g for 3 to 15 minutes so as to separate plasma from RBCs within the container.

As noted above, the flexible conduit 32 extending between the first and second containers contains a precipitating agent 30 as is the compressed second container. In the alternative, only the flexible conduit or the second container contains the precipitating agent. The first bag containing the plasma and separated red blood cells is placed into a standard blood bag press (or manually pressed), pressure is applied to the middle of the bag, and the conduit seal is broken or clamp released so that plasma can flow from the first container 14 to the second container 28. Once the majority of the plasma has been transferred to the second container 28 and the red blood cells approach the region near the outlet port 34 of the first container 10, the transfer conduit 32 is sealed above the container 28 with a standard heat sealer or a clamp. The red blood cells, then, are retained within the first container 14.

To prolong the viability of the retained RBCs and to aid transfer thereof back to the patient or donor, if desired, a red blood cell stabilizer 26 can be transferred from the auxiliary container 24 via a conduit 42 into second inlet port 22 of the first container 14 and mixed gently by inversion. Again, a suitable inline closure or clamp is provided to prevent premature flow from the auxiliary container 24 to the first container 14, which seal is broken or clamp removed to allow mixing of the stabilizing agent 26 with the red blood cells. If desired, then, the red blood cells are transferred to the patient or donor through an outlet port 44 and a RBC return conduit 46. Alternatively, the RBCs are diluted with a suitable buffer (e.g. saline) introduced via an additional part and returned to the patient.

The plasma is mixed with the precipitating agent 30 from the transfer conduit 32 as well as originally present within the second container 28 by kneading and/or gently inverting the second container. That container is then placed in a centrifugal adaptor shown schematically at 48 and centrifuged at 1,000 to 6,000 g for 3 to 15 minutes. Following centrifugation, the second container is removed from the centrifuge adaptor 48 and gently inverted so as to remove the supernatant from the pellet. Preferably, as noted above, the second container is configured so as to define a precipitate receiving compartment 50. Thus, the precipitate or pellet-solution compartment can be physically separated from the supernatant by squeezing the throat 40 of the precipitate collecting compartment and heat sealing or clamping the same so that the pellet material is physically separated from the solution in the remainder of the container. Alternatively, the supernatant is transferred into a third bag and discarded.

The throat 40 can be double sealed and cut between the seals so that a separate pellet solution container is obtained and the factor-poor plasma container discarded or otherwise used. The tube of coagulant protein precipitate or entire second container with supernatant removed may be used to prepare the fibrin sealant immediately. In the alternative, the precipitate container 50 or second container 28 with precipitate therein may be stored at 0 to 4° C. for up to several days or at −20° C. or below for several months.

When it is desired to prepare the fibrin sealant from the precipitate, a buffer solution (e.g. 50 mM Tris-HCl pH 7.4, 150 mM sodium chloride, 250 mM sodium citrate, 200 mM epsilon-aminocaproic acid and 50 mM arginine; e.g. 0.4 ml buffer per ml precipitate) is added to the precipitate container. Thus, if the entire second container is used to store the precipitate and/or produce the fibrin sealant, the buffer solution can be added for example through a port defined in a second container. In the alternative, if the precipitate compartment 50 is separated from the remainder of the second container 28, the buffer solution can be added through a septum 52 defined in the precipitate compartment and covered prior to use with a cap 54. The tube and/or container 28 or 50 is gently kneaded or vortexed to dissolve the precipitate in the buffer solution. In the alternative, the tube can be connected via the outlet port 52 to a vial container, the buffer solution and the precipitate squeezed into the vial and dissolved in the buffer within that vial or other container. The fibrin sealant is prepared by mixing the fibrinogen/Factor XIII precipitate solution with a solution of thrombin and calcium. The dissolved components, calcium and thrombin are transferred into a sterile syringe or container for delivery to the wound or incision site.

As shown in FIG. 2, the present invention, in the alternative, can be a system of relatively rigid tube like containers. Thus, the first container 54 can be an elongated tube which preferably has an hourglass shape so as to be constricted at a central portion 56 thereof or has a flexible band of rubber or plastic at the central portion 56 thereof which can be squeezed together and sealed with a clamp or heat sealed to separate plasma from the red blood cells following centrifugation. In the alternative, the first tube-like container can be symmetrical along the length thereof and the plasma simply decanted from the RBC's perhaps with the assistance of a suction force. Similarly, all or part of the narrow lower portion of the second tube-like container 58 can be constructed from a flexible material to facilitate separation of precipitate from supernatant. Again, the second container 58 can have a narrow throat 60 like portion along the length thereof and bottom most precipitate receiving compartment 62 which may be enlarged in width relative to throat 60. Thus, the second tube like container can have a configuration corresponding to the first tube like container of FIG. 2.

The first container 54 has an anticoagulant 64 disposed therewithin prior to receipt of whole blood. Further, a precipitating agent 66 is disposed within container 58 for precipitating blood coagulation factors from plasma therein. A centrifuge adapter 68 is preferably utilized with the second container when the precipitate receiving compartment 62 is in the form of a narrow tube like structure as shown for example in FIG. 2. The method of collecting the blood coagulation factor in accordance with the present invention is substantially the same with the system of FIG. 2 as with the system of FIG. 1. However, because only a portion or none of the first and second tubes are collapsible, a vacuum or negative pressure is applied to the interior thereof through suction ports 70 so as to minimize air therewithin prior to blood collection and processing.

Referring to FIG. 3 and FIGS. 4a–c, in accordance with yet a further embodiment of the invention, the system for collecting a blood coagulation factor is a multi-compartmented container 72 which is functionally equivalent to a two or more container system as described above with reference to FIGS. 1 and 2. Thus, the multi-compartment container provided in accordance with the present invention includes a first, blood receiving compartment 74 for receiving whole blood from the patient. The whole blood is mixed with an anti-coagulant 76 disposed within the blood collection conduit 78 as well as within the blood receiving compartment 74 of the multi-compartment bag. The blood and anticoagulant mixture is subjected to centrifugal separation so as to separate plasma 80 from RBCs 82 as shown for example in the illustration of FIG. 4b.

The plasma is then passed through a transfer passage into a second compartment of the container. The transfer passage 84 is preferably clamped or has a suitable seal defined therewithin for preventing premature communication between the compartments of the multi-compartment container. Thus, when it is desired to transfer plasma 80 from the first compartment 74 to the second compartment 86, the seal within the transfer passage 84 is broken or clamp provided thereat is removed. The plasma 80 can then be expressed from the first compartment 74 into the second compartment 86 wherein it is mixed with a suitable precipitating agent 88 as shown schematically in FIG. 3.

Figure 3:
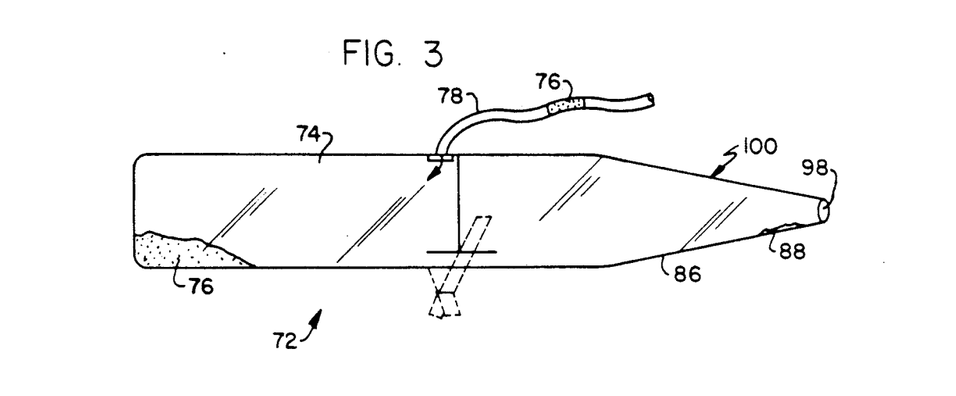
FIG. 3 is a schematic plan view of a multi-compartment system provided in accordance with the present invention.
Figure 4A:
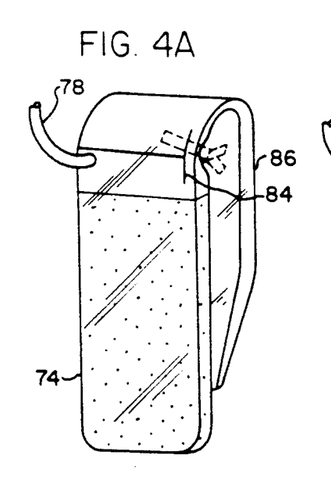
FIGS. 4a–c are schematic perspective views illustrating particular stages of the process of the invention when practiced with the multi-compartment container of FIG. 3.
Figure 4B:
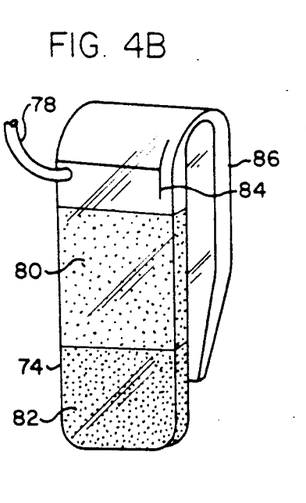
Figure 4C:
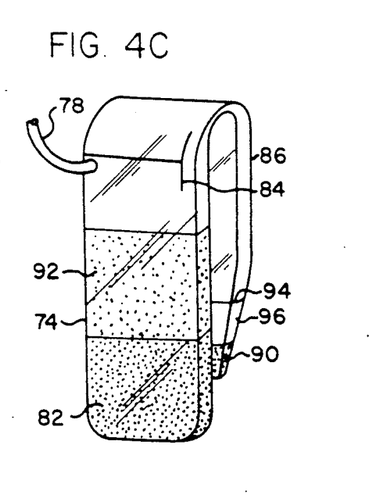

The multi-compartment container 72 is then again subjected to centrifugation so as to separate precipitate 90 from blood coagulation factor poor plasma 92 within the second compartment. The coagulation factor-poor plasma can be returned from the second compartment to the first compartment through the transfer passage 84. Prior to or following such transfer, the lower portion of the second compartment is preferably heat sealed or clamped at 94 so as to physically separate the precipitate from the supernatant in the second compartment 86 of the container 72. The sealed precipitate compartment 96 can then be separated from the remainder of the multi-compartment structure or retained therewith. The precipitate 90 can be removed from the second compartment 86 by accessing the same through a suitable septum 98 or a buffer solution can be added to the precipitate compartment 96 and/or second compartment 86 of the system so as to dissolve the precipitate 90 to allow formation of the fibrin sealant.

As with the embodiment of FIGS. 1 and 2, the RBCs 82 retained within the first compartment 74 of the container can be returned to the patient by any known means.

As shown in particular in FIG. 3, the second compartment of the multi-compartment container is preferably tapered as shown at 100 so as to facilitate collection of the precipitate 90 in a constricted portion of the container and thus facilitate separation of the same from the blood coagulation factor poor-plasma.

While the invention has been described in connection with what is presently considered to be the most practical and preferred embodiments, it is to be understood that the invention is not to be limited to the disclosed embodiments, but, on the contrary, is intended to cover various modifications and equivalent arrangements included within the spirit and scope of the appended claims. Thus, while particular systems have been illustrated in connection with the method of the invention for separating whole blood into plasma and red blood cells and then precipitating blood coagulation factor(s) from the plasma so separated, it is to be understood that various combinations of rigid bottles or tubes and flexible bags can be utilized to collect the precipitate in accordance with the present invention and various configurations for compartmentalizing a single or plural bags can be employed without departing from the novelty of the present invention.

The entire contents of all references cited hereinabove are hereby incorporated by reference.

What is claimed is:

1. A system for collecting a blood coagulation factor comprising a first container means for receiving whole bloood, said first container means having an upper end, a lower end, at least one inlet porot, andd at least one outlet port;

first conduit means for conveying wholle blood to said first container means, ssaidd first conduit means having an end thereof coupled to a said inlet port of said firsst container means;

second container means for receiving pllasma which has been separated from red blood cells in saidd first container means, said second container means having an upper end, a lower end and at least one inlet, said second container means having a first, relatively wide diameter portion adjacent to said upper end thereof, a second relatively narrow portion defined below said first portion for receiving a blood coagulation factor precipitate from the plasma within said second container means and a third relatively wide portion ddefined below said second, relatively narrow portion so that said second, relatively narrow portion defines a relatively narrow passage for precipitate blood coagulation factor from said first portion to said third portion; and second conduit means having a first end thereof coupled to a said outlet port of said first container means and a second end thereof coupled to a said inlet port of said second container means for conveying plasma from said first container means to said second container means.

2. The system as in claim 1, wherein said second container means has at least one outlet port, said system further comprising:

a third container means for receiving one of blood coagulation factor deficient plasma and a blood coagulation factor precipitate from said second container, said third container means having an upper end, a lower end, and at least one inlet port; and third conduit means having a first end thereof coupled to a said outlet port of said second container means and a second end thereof operatively coupled to a said inlet port of said third container means.

3. The system as in claim 2, wherein a said outlet port is defined through said lower end of said second container means and said third container receives a blood coagulation factor precipitate from said second container.

4. A system for collecting a blood coagulation factor comprising:

first containner means for receiving whole blood, said first container means having an upper end, a lower end, at least one inlet port, and at least one outlet port;

first conduit means for conveying whole blood to said first container means, said first conduit means having an end thereof coupled to a said inlet porrt of said first connitainer means;

second container means for receiving plasma which has been separated from red blood cells in saidd first container means, said second container means having an upper end, a lower end and at least one inlet, said second container means having a first, relatively wide diameter portion adjacent to said upper end thereof and a second, rellatively narrow portion defined below said first portion for receiving a bloodd coagulation factor precipitate from the plasma within said second container means, said second, relatively narrow portion of said second container means having a substantially uniform width along the length thereof and terminating at said lower end of said second container means; and second conduit means having a first end thereof coupled to a said outlet port of said first container means and a second end thereof coupled to a said inlet port of said second container means for conveying plasma from said first container means to said second container means.

5. The system as in claim 1, wherein said second container means is a flexible bag, said second portion being heat sealable so as to seal off said third portion from said second portion.

6. The system as in claim 1, wherein said second container means is a flexible bag.

7. A system for collecting a blood coagulation factor comprising:

first container means for receiving wholle bloood, said first container means having an upper end, a lower end, at least one inlet port, and at least one outlet port;

first conduit means for conveying whole bloodd to said first container means, said first conduit means having an end thereof coupled to a said inlet port of said first container means;

second container means for receiving pllasma which has been separated from red blood cells in said first container means, said second container means being a tube, said second container means having an upper end, a lower end and at least one inlet, asid secondd container means having a first, rrelatively wide diameter portion adjacent to said upper end thhereof and a second, relatively narrow portion defined below said first portion for receiving a blood coagulationn factor precipitate from the plasma within said seconddd coontainer means; and second conduit means having a first end thereof coupled to a said outlet port of said first container means and a second end theref coupled to a said inlet port of said second contaner means for conveying plasma from said first container means to said second container means.

8. The system as in claim 7, wherein said second, relatively narrow portion is defined by a constricted portion of said tube.

9. The system as in claim 7, wherein plug means are inserted into said tube, said plug means having a bore defined therein, said bore defining said second, relatively narrow portion of said second container means.

10. The system as in claim 1, wherein said second container means has a blood coagulation factor precipitating agent disposed therewithin.

11. A system for collecting a blood coagulation factor comprising:

first container means for receiving whole blood, said first container means having an upper end, a lower end, at least one inlet port, and at least one outlet port;

first conduit means for conveying whole blood to said first container means, said first conduit means having an end thereof coupled to a said inlet port of said first container means;

second container means for receiving plasma which has been separated from red blood cells in said first container means, said second container means having an upper end, a lower end and at least one inlet, said second container means having a blood coagulation factor precipitating agent disposed therewithin; and second conduit means having a first end thereof coupled to a said outlet port of said first container means and a second end thereof coupled to a said inlet port of said second container means for conveying plasma from said first container means to said second container means.

12. The system as in claim 11, wherein said second container means has at least one outlet port, said system further comprising:

a third container means for receiving one of blood coagulation factor deficient plasma and a blood coagulation factor precipitate from said second container, said third container means having an upper end, a lower end, and at least one inlet port; and third conduit means having a first end thereof coupled to a said outlet port of said second container means and a second end thereof operatively coupled to a said inlet port of said third container means.

13. The system as in claim 12, wherein a said outlet port is defined through said lower end of said second container means and said third container receives a blood coagulation factor precipitate from said second container.

14. The system as in claim 11, wherein said second container means is a flexible bag.

15. The system as in claim 11, wherein said second container means is a rigid container.

16. A device for collecting a blood coagulation factor froom plasma comprising:
  a container means having an upper end, a lower end, at least one inlet port, and a peripheral wall defining, with said upper and lower ends, a plasma receiving compartment, said peripheral wall defining a first, relatively wide diameter portion and a second, relatively narrow diameter portionn below said first, relatively wide portion, ssaid second, relatively narrow portion having a substantially uniform cross-section along the length thereof and terminatinng at the loower end of said container means, and
  a blood coagulation factor precipitating agent disposed within said plasma receiving compartment.

17. The device as in claim 16, further comprising at least one outlet port.

18. The device as in claim 17, wherein said outlet port is defined through said upper end of said container means.

19. The device as in claim 17, wherein said outlet port is defined through said lower end of said container means.

20. The device as in claim 16, wherein said container means is a flexible bag.

21. The device as in claim 16, wherein said container means is a tube.

22. A device for collecting a blood coagulation factor from plasma comprising:
  a container means having an upper end, a lower end, at least one inlet port, and a peripheral wall defining, with said upper and lower ends, a plasma receiving compartment, said peripheral wall defining a first, relatively wide diameter portion and a second, relatively narrow diameter portion below said first, relatively wide portion; and
  a blood coagulation factor precipitating agent disposed within said plasma receiving compartment.

23. The device as in claim 22, comprising a third, relatively wide diameter portion below said second, relatively narrow diameter portion.

24. The device as in claim 23, further comprising at least one outlet port.

25. The device as in claim 24, wherein said outlet port is defined through said upper end of said container means.

26. The device as in claim 24, wherein said outlet port is defined through said lower end of said container means.

27. The device as in claim 22, wherein said container means is a flexible bag.

28. The device as in claim 22, wherein said container means is a tube.

29. A method of collecting at least one blood clotting factor comprising:
  i) drawing a sample of whole blood from a patient into a first container means having disposed therewithin an amount of an anticoagulant sufficient to prevent clotting of said blood sample;
  ii) mixing said blood sample with said anticoagulant;
  iii) separating red blood cells present in said blood sample from plasma of said blood sample;
  iv) transferring said plasma to a second container means via a conduit coupled to an outlet port of said first container means and an inlet port of said second container means, said second container means or said conduit containing an amount of a pharmaceutically acceptable protein precipitating agent sufficient to effect precipitation of fibrinogen and Factor XIII present in said plasma;
  v) mixing said plasma with said precipitating agent so that a fibrinogen/Factor XIII-containing precipitate, and a supernatant, are formed; and
  vi) separating said precipitate from said supernatant.

30. The method as in claim 29 wherein said precipitating agent is a zinc (II) salt.

31. The method as in claim 29 further comprising the steps of dissolving said separated precipitate in a pharmaceutically acceptable buffer whereby a solution is formed and contacting said solution with thrombin under conditions such that a fibrin sealant is formed.

32. The method as in claim 31 wherein formation of said fibrin sealant is effected at a body site.

33. The system as in claim 4, wherein said second container means is substantially free from means filtering material flowing therewithin whereby blood coagulation factor precipitate can be collected at said lower end of said second container means.

34. A system as in claim 4, wherein said second container means has at least one outlet port, said system further comprising:
  a third container means foor receiving one of blood coagulation factor deficient plasma andd a blood cooagulation factor precipitate from said second container, said third container means having an upper end, a lower end, and at least one inlet port; and
  third conduit means haing a first end thereoof coupled to a said outlet port of said second container means and a second end thereof operatively coupled to a said inlet port of said third container means.

35. The system as in claim 34, wherein a said outlet port is defined through said lower end of said second container means and said third container receives a blood coagulation factor precipitate from said second container.

36. The system as in claim 4, wherein said second container meanss is a flexible bag.

37. The system as in claim 7, wherein said second container means has a blood coagulation factor precipitating agent disposed thherewithin.

* * * * *

UNITED STATES PATENT AND TRADEMARK OFFICE
CERTIFICATE OF CORRECTION

PATENT NO. : 5,030,215

DATED : July 9, 1991

INVENTOR(S) : MORSE ET AL

It is certified that error appears in the above-identified patent and that said Letters Patent is hereby corrected as shown below:

Column 1, line 45, "hopsit.las" should be --hospitals--.

Column 8, line 12, "FIGS i and 2" should be --FIGS 1 and 2--;
 line 45, "bloood" should be --blood--;
 line 47, "porot" should be --port-- and "andd" should be --and--;
 line 49, "wholle" should be --whole--;
 line 50, "ssaidd" should be --said--;
 line 52, "firsst" should be --first--;
 line 53, "pllasma" should be --plasma--;
 line 54, "saidd" should be --said--;
 line 63, "ddefined" should be --defined--.

UNITED STATES PATENT AND TRADEMARK OFFICE
CERTIFICATE OF CORRECTION

PATENT NO. : 5,030,215

DATED : July 9, 1991

INVENTOR(S) : MORSE ET AL

It is certified that error appears in the above-identified patent and that said Letters Patent is hereby corrected as shown below:

Column 9, line 28, "containner" should be --container--;

line 34, "porrt" should be --port--;

line 35, "conntainer" should be --container--;

line 37, "saidd" should be --said--;

line 42, "rellatively" should be --relatively--;

line 44, "bloodd" should be --blood--;

line 64, "wholle bloood" should be --whole blood--.

Column 10, line 1, "bloodd" should be --blood--;

line 5, "pllasma" should be --plasma--;

line 10, "asid" should be --said--, "secondd" should be --second-- and "rrela-" should be --rela-- -;

line 12, "thhereof" should be --thereof-- line 15, "secondd" should be --second-- and "coontainer" should be --container--.

UNITED STATES PATENT AND TRADEMARK OFFICE
CERTIFICATE OF CORRECTION

PATENT NO. : 5,030,215

DATED : July 9, 1991

INVENTOR(S) : MORSE ET AL

It is certified that error appears in the above-identified patent and that said Letters Patent is hereby corrected as shown below:

Column 11, line 11, "toor" should be --tor-- and "froom" should be --from--;

line 16, "sec-" should be --se---;

line 17, "ond should be --cond-- and "portionn" should be --portion--;

line 18, "ssaid" should be --said--;

line 21, "terminatinng" should be --terminating-- and "loower" should be --lower--.

Column 12, line 42, "andd" should be --and--; and line 61, "thherewithin" should be --therewithin--.

Signed and Sealed this

Fifteenth Day of December, 1992

Attest:

DOUGLAS B. COMER

Attesting Officer      Acting Commissioner of Patents and Trademarks